(12) United States Patent
Tate et al.

(10) Patent No.: US 7,851,760 B2
(45) Date of Patent: Dec. 14, 2010

(54) CONTROL AND OPTIMIZATION OF PROCESS FOR MAKING ETHYLENE OXIDE

(75) Inventors: James D. Tate, Lake Jackson, TX (US); Louise A. Mahoney, Lake Jackson, TX (US); Vernon D. Darling, Prarieville, LA (US)

(73) Assignee: Dow Global Technology Inc.

( * ) Notice: Subject to any disclaimer, the term of this patent is extended or adjusted under 35 U.S.C. 154(b) by 0 days.

(21) Appl. No.: 12/377,459

(22) PCT Filed: Aug. 30, 2007

(86) PCT No.: PCT/US2007/019097

§ 371 (c)(1),
(2), (4) Date: Oct. 22, 2009

(87) PCT Pub. No.: WO2008/030386

PCT Pub. Date: Mar. 13, 2008

(65) Prior Publication Data

US 2010/0032570 A1    Feb. 11, 2010

Related U.S. Application Data

(60) Provisional application No. 60/841,767, filed on Sep. 1, 2006.

(51) Int. Cl.
*G01J 5/02* (2006.01)
(52) U.S. Cl. .................................................... 250/340
(58) Field of Classification Search ................... 250/340
See application file for complete search history.

(56) References Cited

U.S. PATENT DOCUMENTS

| | | | |
|---|---|---|---|
| 2,279,469 A | 4/1942 | Law et al. | |
| 2,279,470 A | 4/1942 | Law et al. | |
| 3,119,837 A | 1/1964 | Kingsley et al. | |
| 5,102,848 A | 4/1992 | Soo et al. | |
| 5,173,749 A | 12/1992 | Tell et al. | |
| 5,187,140 A | 2/1993 | Thorsteinson et al. | |
| 5,840,932 A * | 11/1998 | Evans et al. | 549/512 |
| 6,150,661 A | 11/2000 | McCaul et al. | |
| 6,258,978 B1 | 7/2001 | Kitchen et al. | |

(Continued)

FOREIGN PATENT DOCUMENTS

EP          3462          1/1979

(Continued)

OTHER PUBLICATIONS

Schmalz et al., "Anionic polymerization of ethylene oxide in the presence of the phosphazene based BuP4-Kinetic Investigations using in-situ FT-NIR spectroscopy and MALDI-ToF MS," 2003, Macromolecular Chemistry and Physics—Wiley Online Library, vol. 204, No. 8, pp. 1056-1071.*

(Continued)

*Primary Examiner*—David P Porta
*Assistant Examiner*—Kiho Kim

(57) ABSTRACT

The invention pertains to a method for controlling the Limiting Oxygen Value (LOV) of a reactor for producing ethylene oxide using a tunable diode laser. The sample to be tested is extracted. A method for controlling oxygen analyzer safety shutdown for a reactor for producing ethylene oxide using a tunable diode laser is also described.

3 Claims, 3 Drawing Sheets

U.S. PATENT DOCUMENTS

| | | | |
|---|---|---|---|
| 6,372,925 | B1 | 4/2002 | Evans et al. |
| 6,465,592 | B1 | 10/2002 | Kitada et al. |
| 6,511,938 | B1 | 1/2003 | Liu et al. |
| 6,638,434 | B2 * | 10/2003 | Otsuki .................. 210/748.08 |
| 6,640,199 | B1 | 10/2003 | Goldstein et al. |
| 6,717,001 | B2 | 4/2004 | Evans et al. |
| 6,859,766 | B2 | 2/2005 | Von Drasek et al. |
| 7,005,645 | B2 | 2/2006 | Von Drasek et al. |
| 7,022,992 | B2 | 4/2006 | Grant et al. |
| 7,115,775 | B2 | 10/2006 | Buschulte et al. |
| 7,166,843 | B2 | 1/2007 | May |
| 7,248,755 | B2 | 7/2007 | Sappey et al. |
| 7,389,027 | B2 | 6/2008 | Sappey et al. |
| 7,469,092 | B2 | 12/2008 | Sappey et al. |
| 2002/0031737 | A1 | 3/2002 | Von Drasek et al. |
| 2003/0132389 | A1 | 7/2003 | Von Drasek et al. |
| 2003/0160174 | A1 | 8/2003 | Grant et al. |
| 2004/0097774 | A1 | 5/2004 | Hall et al. |
| 2004/0138499 | A1 | 7/2004 | Buschulte et al. |
| 2004/0191712 | A1 | 9/2004 | Thomson et al. |

FOREIGN PATENT DOCUMENTS

GB 0767751 2/1957

OTHER PUBLICATIONS

Hanson et al., Sensors for Advanced Combustion Systems, Global Climate and Energy Project, Stanford University, 2004.

Kirk-Othmer, "Encyclopedia of Chemical Technology", 4th ed. (1994), vol 9, pp. 915-959.

* cited by examiner

CONTROL AND OPTIMIZATION OF PROCESS FOR MAKING ETHYLENE OXIDE

CROSS REFERENCE TO RELATED APPLICATIONS

This application is a 371 of PCT/US2007/019097 filed Aug. 30, 2007, which claims the benefit of U.S. Provisional Application Ser. No. 60/841,767, filed Sep. 1, 2006.

BACKGROUND OF THE INVENTION

The instant invention relates to processes for the manufacture of ethylene oxide. The production of ethylene oxide by the reaction of oxygen or oxygen-containing gases with ethylene in the presence of a silver-containing catalyst at elevated temperature is a key process in the chemical industry. Due to the flammable nature of oxygen, these processes rely on precise and accurate control of oxygen, and particularly, the "Limiting Oxygen Value" ("LOV"), also known as the Maximum Allowable Oxygen Concentration "(MAOC"). The LOV is the oxygen concentration at which a combustion reaction will propagate through ethylene oxide process gas. Those of skill in the art are familiar with formulas for the calculation of LOV. Using too much oxygen can result in a catastrophic ignition, while using too little can result in poor yield. Independent reactor inlet and outlet oxygen analyzers are also used for automatic safety shutdown and isolation of oxygen feeds. If the capability to monitor inlet oxygen concentration continuously is lost, oxygen and hydrocarbon feeds must be immediately shut off. If the capability to monitor outlet oxygen concentration continuously is lost, either (a) the affected reactor must be shut down immediately or (b) the inlet oxygen concentration must be kept below the outlet operating limit. If alternative (b) is chosen, the reactor must be shut down immediately if the inlet oxygen concentration exceeds an offset from the LOV to ensure that a safety margin can be maintained. The size of the offset depends on the system geometry and past history of decompositions. For example, the shut down could be triggered where the oxygen concentration exceeds outlet LOV+1 vol % (based on LOV calculations before loss of capability to monitor). (Many commercial ethylene oxide plants would choose not to operate under this option (b). Therefore, it is very important to control the LOV at the reactors with a high degree of accuracy and precision. In fact, most ethylene oxide facilities demand that analyzer systems and instrumentation have full redundancy.

Currently, the best practice in the industry is to use an oxygen measurement based on a paramagnetic analyzer. Limitations in the measurement itself can dramatically affect the ability to control the LOV at its optimum, and therefore limit the overall efficiency and yield of an ethylene oxide plant. There are several drawbacks to use of paramagnetic analyzers for controlling LOV:

(1) Many non-oxygen components of reaction system gas depress the oxygen concentration indicated by a paramagnetic analyzer, causing a paramagnetic offset. There are two ways to compensate for this offset. The first is to calibrate concentration at the midpoint of the range of the non-target gases. A disadvantage to this approach is that the compensation will be an average of the offset and the uncertainty of the measurement increases. The second is to compensate with "live" input from a gas chromatograph or gas chromatograph/mass spectrometer. Disadvantages to this approach are that the data is not real-time and that the reliability of the mass spectrometer is not as high as using other methods.

(2) Oxygen is reactive. Questions arise concerning sample integrity when the sample is transported through 10-100 meters of tubing to an analyzer in an analyzer shelter, such as with the paramagnetic analyzers.

(3) The process temperatures in the ethylene oxide streams can be as high as 330° C., but the temperature limit for a paramagnetic analyzer is about 130° C. Thus, the sample temperature must be reduced prior to analysis.

(4) The process pressures in the ethylene oxide streams can be as high as 350 psig, whereas the pressure limit for a paramagnetic analyzer is about 50 psig. Thus, the sample pressure must be decreased prior to analysis.

(5) The paramagnetic analyzers become fouled by the solids/liquids in the streams, causing mirrors to coat and cells to short. Thus, the samples can destroy or compromise the measurements.

(6) The paramagnetic analyzers take time to transport the sample to the sheltered analyzer and take additional time to condition the sample (reduce temperature, decrease pressure).

(7) The paramagnetic analyzers cell vents are connected to a cell vent header and require pressure compensation. Variability in the pressure compensation leads to uncertainty in the oxygen measurements.

All of these drawbacks to paramagnetic analyzers result in introducing variability into the control of LOV. Thus, there is a need in the art for a method to more quickly, accurately and precisely measure oxygen in ethylene oxide processes than the best practice in use today.

The development of the tunable near-infrared diode laser and absorption spectroscopy approach for the determination of oxygen, carbon monoxide, and oxides of nitrogen in the combustion gas from a coal fired utility boiler, a waste incinerator as well as from jet engines are summarized in Section II.4.3, Sensors for Advanced Combustion Systems, Global Climate & Energy Project, Stanford University, 2004, by Hanson et al. In Thompson et al., US Patent Application Publication US 2004/0191712 A1, a tunable near-infrared diode laser and absorption spectroscopy system to was applied to combustion applications in the steelmaking industry.

Kitchen, et al., U.S. Pat. No. 6,258,978, discloses a method of making vinyl acetate by contacting ethylene, acetic acid, and oxygen in the presence of a catalyst to produce an outlet stream. The concentration of oxygen in the outlet stream is maintained at or near its flammability limit. Kitchen points out that paramagnetic analyzers cannot be used where high temperature and pressure conditions are encountered, for example, adjacent to the reactor outlet.

SUMMARY OF THE INVENTION

The instant invention is a solution, at least in part, to the above-stated problem of the need for a more precise, reliable and representative analysis of oxygen concentrations in an ethylene oxide reaction system. Singly or in combination, and preferably in combination, the instant invention can also solve the problem of the need for a more reliable and representative oxygen analyzer safety shutdown system. The instant invention uses tunable near-infrared diode laser and absorption spectroscopy technology for the determination of oxygen concentration, in the inlet and outlet of an ethylene oxide reactor. The method is performed by sample extraction.

More specifically, the invention is a method for control of a Limiting Oxygen Value (LOV) of a reactor for producing ethylene oxide, the reactor having an inlet and/or outlet, comprising the steps of: (a) extracting a process sample through a close-coupled extractive sample loop wherein an analyzer is located in proximity to the sampling point; (b) directing a wavelength modulated beam of near infrared light from a tunable diode laser through a gas cell containing the process sample to a near infrared light detector to generate a detector signal; (c) analyzing the detector signal for spectroscopic absorption at wavelengths characteristic for oxygen to determine its concentration in the sample; and optionally (d) adjusting the oxygen level in the ethylene oxide reactor inlet and/or outlet in response to the concentration of the oxygen of step (c).

The invention also includes a method for control of an oxygen analyzer safety shutdown of oxygen feed and reaction system of a reactor for producing ethylene oxide, the reactor having an inlet and/or outlet, comprising the steps of: (a) extracting a process sample through a close-coupled extractive sample loop wherein an analyzer is located in proximity to the sampling point; (b) directing a wavelength modulated beam of near infrared light from a tunable diode laser through a gas cell containing the process sample to a near infrared light detector to generate a detector signal; (c) analyzing the detector signal for spectroscopic absorption at wavelengths characteristic for oxygen to determine its concentration in the sample; and optionally (d) adjusting the oxygen level in the ethylene oxide reactor inlet and/or outlet in response to the concentration of the oxygen of step (c) or shutting down the oxygen feed and reaction system if the oxygen measurement exceeds an oxygen concentration shutdown setpoint.

In one embodiment, the wavelength of the near infrared light from the tunable diode laser is in the range of from about 760-764 nm.

DETAILED DESCRIPTION

The reaction conditions for carrying out the vapor phase oxidation of ethylene with molecular oxygen are well-known and extensively described in the prior art. This applies to reaction conditions, such as, temperature, pressure, residence time, concentration of reactants, diluents (e.g., nitrogen, methane and $CO_2$), inhibitors (e.g., ethylene dichloride) and the like. Examples of inhibitors, such as nitrogen oxides and nitrogen oxides generating compounds are described in Law, et al., U.S. Pat. Nos. 2,279,469 and 2,279,470, incorporated herein by reference. Other gases fed to the reaction may include a gaseous efficiency-enhancing member of a redox-half reaction pair such as NO, $NO_2$, $N_2O_3$, $N_2O_4$, $N_2O_5$ or any gaseous substance capable of forming one of the aforementioned gases, particularly NO and $NO_2$, under epoxidation conditions, and mixtures thereof with one or more of $PH_3$, CO, $SO_3$, $SO_2$, $P_2O_5$, and $P_2O_3$. See, e.g., EP 3642 and Liu et al., U.S. Pat. No. 6,511,938, each incorporated herein by reference.

In addition, the desirability of recycling unreacted feed, or employing a single-pass system, or using successive reactions to increase ethylene conversion by employing reactors in series arrangement can be readily determined by those skilled in the art. The particular mode of operation selected will usually be dictated by process economics.

Generally, the commercially-practiced processes for producing ethylene oxide are carried out by continuously introducing a feed stream containing ethylene and oxygen to a catalyst-containing reactor at a temperature of from about 200 to 300° C., and a pressure which may vary from about 10 atmospheres to about 30 atmospheres depending upon the mass velocity and productivity desired. Most commercially practiced processes operate at temperature greater than about 210° C. and at a pressure above 15 barg. Residence times in large-scale reactors are generally on the order of about 5-15 seconds (or Gas Hour Space Velocities around 3000 $hr^{-1}$ to 7000 $hr^{-1}$). Oxygen may be supplied to the reaction in an oxygen-containing stream, such as air or as commercial oxygen. The resulting ethylene oxide is separated and recovered from the reaction products using conventional methods. A usual gas recycle encompasses carbon dioxide recycle in the concentrations, e.g., of about 0.5 to 10 volume percent.

An excellent discussion on ethylene oxide, including a detailed description of commonly used manufacturing process steps, for both air and oxygen based processes is found in Kirk-Othmer's *Encyclopedia of Chemical Technology*, 4$^{th}$ Ed. (1994) Volume 9, pages 915 to 959). Typical air and oxygen process test conditions are described in U.S. Pat. Nos. 5,187,140 and 5,102,848, each incorporated herein by reference.

Figure 1:
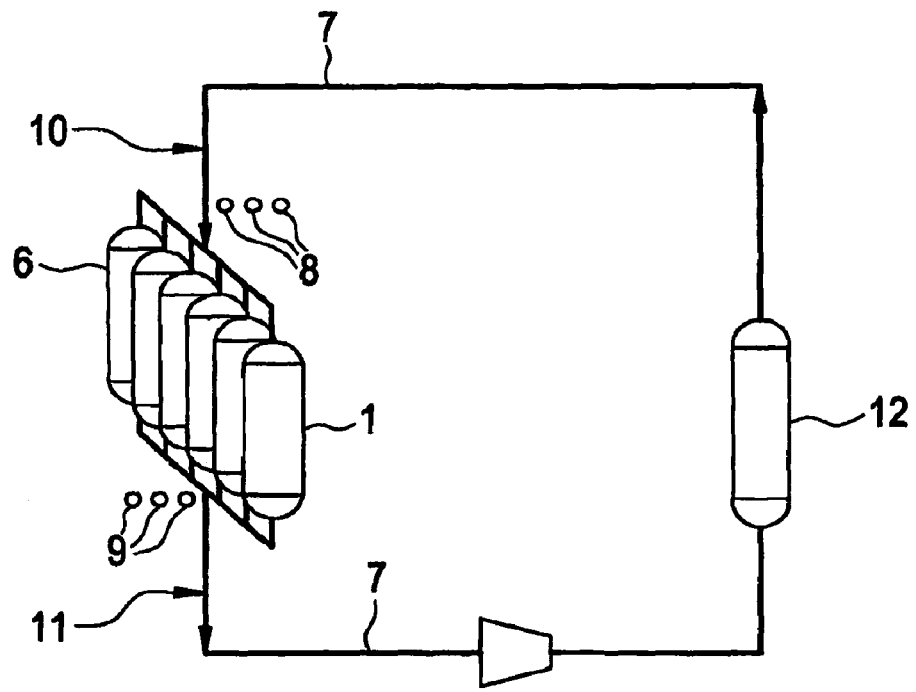
FIG. 1 is a schematic of a generic oxygen analyzer system for ethylene oxide reactors.

FIG. 1 shows the ethylene oxide reactor(s) 1 through 6 and cycle gas loop 7, oxygen supply inlet 10, ethylene supply inlet 11, and absorber 12. The desired locations at which to sample and to measure oxygen concentration (sampling points) are located at the inlet 8 and outlet 9 of the reactors. The desire is to measure oxygen concentration at the common reactor inlet piping 8 and on the common reactor outlet piping 9. Both measurements should be as close as possible to the reactor for the most representative measurement.

Figure 2:
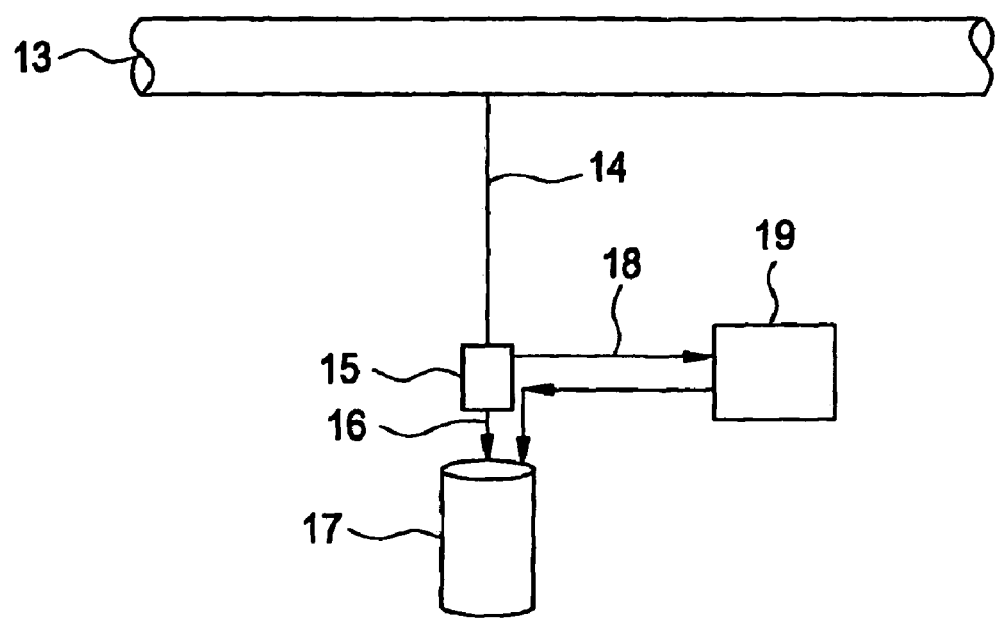
FIG. 2 is a schematic of a conventional oxygen analyzer sample system with respect to the ethylene oxide reactors.

FIG. 2 shows a traditional extractive oxygen analyzer sample system. The process piping 13 is representative of all connections for the reactor inlet 8 and reactor outlet 9 oxygen analyzers depicted in FIG. 1. A fast loop sample 14 transports the sample about 50 or more meters from the sampling location to an entrainment separation device 15 which conditions the sample for analysis. The bulk of the fast loop 16 continues on to a low pressure vessel 17. A small sample stream 18 is extracted from the entrainment separation device 15 and transported to the paramagnetic oxygen analyzer 19. Then the sample stream 20 is returned to the low pressure vessel 17.

Figure 3:
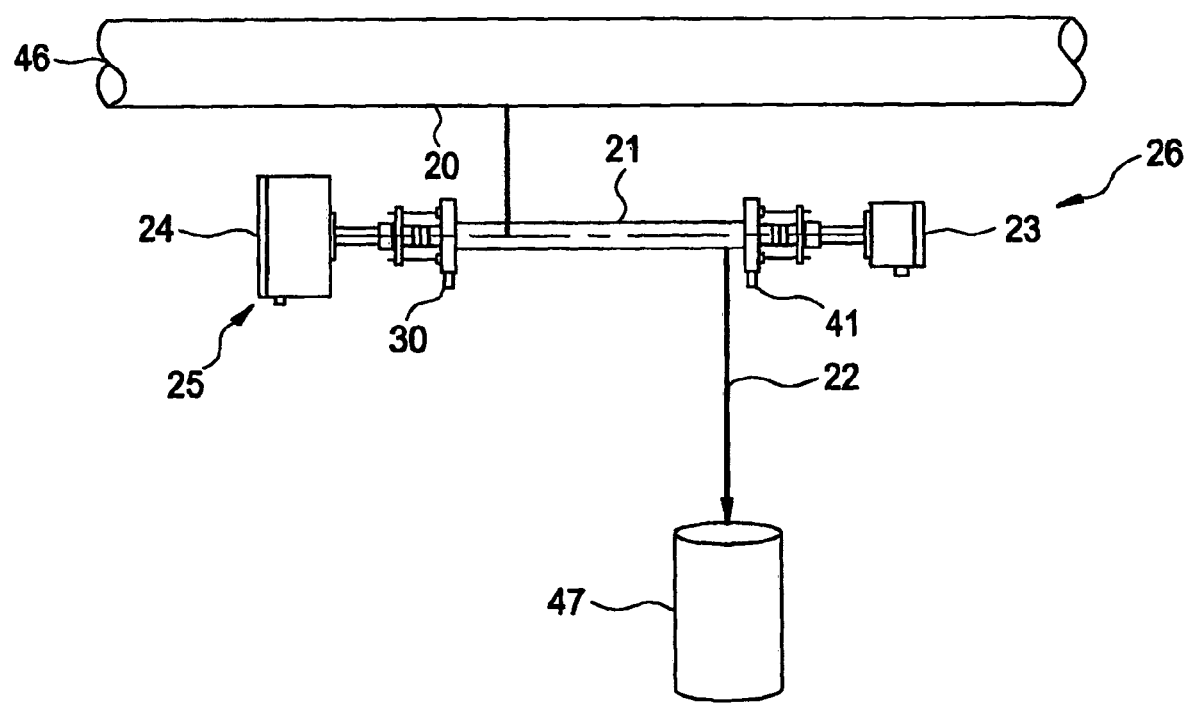
FIG. 3 is a schematic of one embodiment of the tunable diode laser sample cell being close-coupled, near the cycle gas piping for improved speed of response.

FIG. 3 depicts one embodiment of a close-coupled tunable diode laser oxygen analyzer sample system 25 and light detector system 26. The process piping 46 is representative of all connections for the reactor inlet 8 and reactor outlet 9 oxygen analyzers depicted in FIG. 1. A fast loop sample 20 transports the sample about 0 to about 5 meters from the sampling point to the tunable diode laser sample cell 21. The fast loop sample 22 is then returned to the low pressure vessel 47 and the process. The laser transmitter 23 emits a beam of infrared light which traverses the length of the sample cell 21 and is captured by the receiver 24 for a nearly real-time measurement of the sample (cycle gas) oxygen concentration. Alignment plates 30 and 41 are shown for reference.

Figure 4:
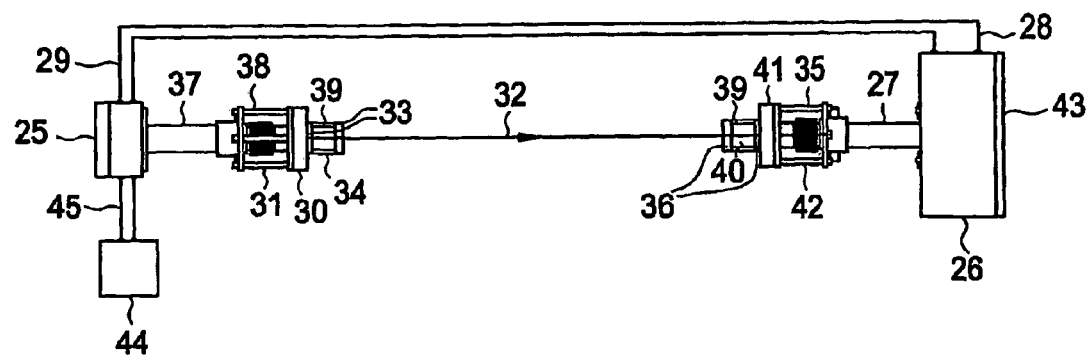
FIG. 4 is a detailed view of a preferred tunable diode laser-spectroscopy apparatus for use in the instant invention.

Referring now to FIG. 4, there is shown a more detailed view of the tunable diode laser system 25 and light detector system 26 shown in FIG. 3. The system shown in FIG. 4 includes a laser module 28 containing the tunable diode laser. A control unit 29 contains the central processing unit programmed for signal processing as well as the temperature and current control for the tunable diode laser and a user interface and display. Alignment plate 30 and adjustment rods 31 allow alignment of the laser beam 32. Windows 33 are mounted in a pipe flange 34. The space 35 between the windows 33 is purged with nitrogen under pressure. The flange 34 is mounted through the wall of the cycle gas pipe (not shown).

Referring still to FIG. 4, the laser beam 32 is passed through windows 36 to a near infrared light detector 37. The windows 36 are mounted across a pipe for an in situ measurement. The space 40 between the windows 36 is purged with nitrogen under pressure. The flange 39 is mounted through the wall of the cycle gas pipe (not shown). Alignment plate 41 and adjustment rods 42 allow alignment of the detector optics with the laser beam 32. Detector electronics 43 are in electrical communication with the control unit 29 by way of cable 28. The control unit 29 is also in electrical communication with the process control system 44 (by way of electrical cables 45) for controlling the reactor 10. The optical path length of the laser beam 32 is the length of cell sample 21 for close coupled installations (FIG. 3). The system shown in FIG. 3 is commercially available from Analytical Specialties of Houston, Tex.

The system shown in FIG. 4 operates by measuring the amount of laser light that is absorbed (lost) as it travels through the sample of cycle gas. Oxygen has a spectral absorption that exhibits unique fine structure. The individual features of the spectra are seen at the high resolution of the tunable diode laser module 28. The tunable diode laser 28 is modulated (that is scanned or tuned from one wavelength to another) by controlling its input current from the control unit 29.

Figure 5:
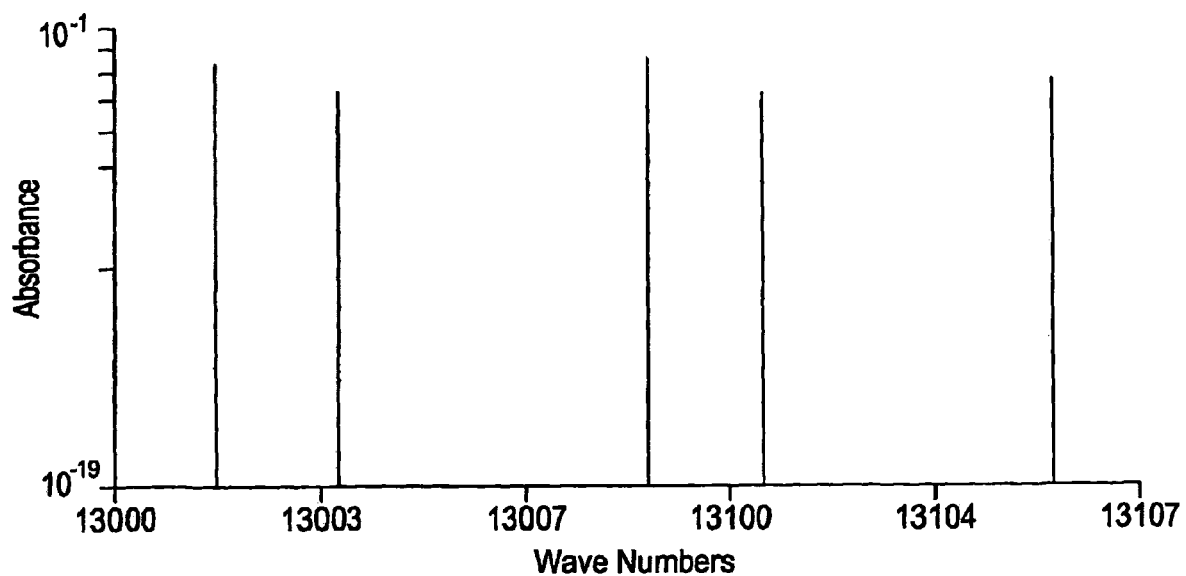
FIG. 5 is spectra collected using the system of the instant invention showing fine structure absorbance in the wavelength region characteristic for oxygen absorbance of near infrared light generated by a tunable diode laser.

Referring now to FIG. 5, therein is shown a spectrum in the region where oxygen absorbs the modulated beam of near infrared light from the tunable diode laser. The absorbance shown in FIG. 5 is proportional to the concentration of oxygen in the process gas.

Referring again to FIG. 1, the oxygen LOV control can be controlled to optimize the oxygen concentrations in the ethylene oxide cycle gas in response to the tunable diode laser spectroscopic analysis of oxygen outlined above.

While the instant invention has been described above according to its preferred embodiments, it can be modified within the spirit and scope of this disclosure. This application is therefore intended to cover any variations, uses, or adaptations of the instant invention using the general principles disclosed herein. Further, the instant application is intended to cover such departures from the present disclosure as come within the known or customary practice in the art to which this invention pertains and which fall within the limits of the following claims.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Of course, variations of those preferred embodiments will become apparent to those of ordinary skill in the art upon the foregoing description. The inventors expect skilled artisans to employ such variations as appropriate, and the inventors intend the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for control of a Limiting Oxygen Value (LOV) of a reactor for producing ethylene oxide, the reactor having an inlet and/or outlet, comprising the steps of: (a) extracting a process sample through a close-coupled extractive sample loop wherein an analyzer is located in proximity to the sampling point; (b) directing a wavelength modulated beam of near infrared light from a tunable diode laser through a gas cell containing the process sample to a near infrared light detector to generate a detector signal; (c) analyzing the detector signal for spectroscopic absorption at wavelengths characteristic for oxygen to determine its concentration in the sample; and optionally (d) adjusting the oxygen level in the ethylene oxide reactor inlet and/or outlet in response to the concentration of the oxygen of step (c).

2. A method for control of an oxygen analyzer safety shutdown of oxygen feed and reaction system of a reactor for producing ethylene oxide, the reactor having an inlet and/or outlet, comprising the steps of: (a) extracting a process sample through a close-coupled extractive sample loop wherein an analyzer is located in proximity to the sampling point; (b) directing a wavelength modulated beam of near infrared light from a tunable diode laser through a gas cell containing the process sample to a near infrared light detector to generate a detector signal; (c) analyzing the detector signal for spectroscopic absorption at wavelengths characteristic for oxygen to determine its concentration in the sample; and optionally (d) adjusting the oxygen level in the ethylene oxide reactor inlet and/or outlet in response to the concentration of the oxygen of step (c) or shutting down the oxygen feed and reaction system if the oxygen measurement exceeds an oxygen concentration shutdown setpoint.

3. The method of claim 1 or 2, wherein the wavelength of the near infrared light from the tunable diode laser is in the range of from about 760-764 nm.

* * * * *